United States Patent [19]

Sherman, Jr. et al.

[11] 4,262,142

[45] Apr. 14, 1981

[54] HYDROFORMYLATION OF ETHYLENE WITH HIGHER OLEFINS

[75] Inventors: Paul D. Sherman, Jr., South Charleston, W. Va.; Stephen C. Winans, Kingsland, Ga.; Dennis G. Morrell, Audubon, Pa.

[73] Assignee: Union Carbide Corporation, New York, N.Y.

[21] Appl. No.: 108,282

[22] Filed: Dec. 28, 1979

[51] Int. Cl.³ .............................................. C07C 45/50
[52] U.S. Cl. ..................................... 568/454; 568/909
[58] Field of Search ........................ 568/454, 882, 909

[56] References Cited

U.S. PATENT DOCUMENTS

| | | | |
|---|---|---|---|
| 3,527,809 | 9/1970 | Pruett et al. | 568/454 |
| 3,917,661 | 11/1975 | Pruett et al. | 568/454 |
| 4,143,075 | 3/1979 | Bryant | 568/454 |
| 4,148,830 | 4/1979 | Pruett et al. | 568/454 |

FOREIGN PATENT DOCUMENTS

| | | | |
|---|---|---|---|
| 821637 | 10/1973 | Belgium | 568/454 |
| 1086100 | 10/1964 | United Kingdom | 568/454 |
| 1120277 | 7/1965 | United Kingdom | 568/454 |

*Primary Examiner*—Werren B. Lone
*Attorney, Agent, or Firm*—Eugene C. Trautlein; Gerald L. Coon

[57] ABSTRACT

In a rhodium-catalyzed hydroformylation process employing olefin reactants having from 3 to 20 carbon atoms to produce products rich in normal aldehydes, the efficiency of the catalyst in producing such products is substantially uneffected and propionaldehyde is also produced by employing ethylene as a coreactant along with the olefin.

5 Claims, No Drawings

HYDROFORMYLATION OF ETHYLENE WITH HIGHER OLEFINS

FIELD OF THE INVENTION

This invention relates to the hydroformylation of olefins to produce aldehydes.

BACKGROUND OF THE INVENTION

Processes for forming an aldehyde by the reaction of an olefin with carbon monoxide and hydrogen are known as hydroformylation processes or oxo processes. For many years, all commercial hydroformylation reactions employed cobalt carbonyl catalysts which required relatively high pressures (often on the order of 100 atmospheres of higher) to maintain catalyst stability. Such processes are described, for example, in British Patent Specification No. 1,120,277 which, inter alia, discloses the coreaction of ethylene and propylene. The data in this British Patent Specification indicates that the presence of ethylene negatively influences the production of butyraldehydes from the propylene in terms of the weight of aldehydes produced in a given time using a given quantity of catalyst.

U.S. Pat. No. 3,527,809 discloses a significantly improved hydroformylation process whereby alpha-olefins are hydroformylated with carbon monoxide and hydrogen to produce aldehydes in high yields at low temperature and pressures. The normal to iso-(or branched-chain) aldehyde isomer ratio of the product aldehydes is high. This process employs certain rhodium complex catalysts and operates under defined reaction conditions to accomplish the olefin hydroformylation. Since this process operates at significantly lower pressures than required theretofore in the prior art as typified by the aforementioned British Patent Specification, substantial advantages are realized including lower initial capital investment and lower operating costs. Further, the more desirable normal aldehyde isomer can be produced in high yields. The rhodium catalyzed process of U.S. Pat. No. 3,527,809 is at times referred to as the "low pressure oxo process" and is so referred to herein.

Several patents and patent applications disclose improvements in the low pressure oxo process. These includes U.S. Pat. No. 3,917,661, U.S. Pat. No. 4,148,830, U.S. Pat. No. 4,143,075, Belgium Pat. No. 856,542, Belgium Pat. No. 853,377, Belgium Pat. No. 863,267, Belgium Pat. No. 863,268, U.S. patent applications Ser. No. 051,189, filed June 22, 1979, U.S. patent application Ser. No. 079,884, filed Sept. 28, 1979, U.S. patent application Ser. No. 040,913 filed May 21, 1979, and U.S. patent application Ser. No. 090,140, filed Nov. 1, 1979. Other patents relating to the low pressure oxo process include Belgium Pat. No. 821,637.

However, none of the above-mentioned patents or applications relating to the low pressure oxo process specifically disclose the use of ethylene and a higher olefin in combination in that process or suggest that the use of such coreactants in that process would be free of the production limitations implied by the data in British Patent Specification No. 1,120,277.

SUMMARY OF THE INVENTION

This invention provides an improvement in a process for the production of oxygenated products comprising aldehydes having a high normal/iso aldehyde ratio which process comprises: (1) forming a reaction mixture containing (a) an alpha olefinic hydrocarbon having from 3 to 20 carbon atoms, (b) carbon monoxide, (c) hydrogen, (d) a catalytic quantity of a complex catalyst consisting essentially of rhodium in complex combination with (i) carbon monoxide and (ii) a triorgano phosphorus ligand of the group consisting of trialkylphosphites, tricycloalkylphosphites, triarylphosphites and triarylphosphines; each organic moiety thereof having up to 18 carbon atoms, and said triorgano phosphorus ligand processing a Δ HNP value of at least about 425, and (e) at least 2 moles of free ligand as defined above per mole of rhodium; (2) maintaining the reaction mixture at a temperature in the range of from about 50° C. to 145° C.; at a total pressure of carbon monoxide and hydrogen of less than 450 psia, and a partial pressure attributable to carbon monoxide no greater than about 75 percent of said total pressure; and (3) thereby reacting said olefinic hydrocarbon with said carbon monoxide and hydrogen with the formation of said oxygenated products comprising aldehydes having a high normal/iso aldehyde ratio. The improvement provided by this invention consists in including in the reaction mixture ethylene and additional carbon monoxide and hydrogen in amounts at least sufficient to react with the ethylene and reacting the ethylene with said carbon monoxide and hydrogen with the formation of propionaldehyde in addition to and concurrently with said oxygenated products comprising aldehydes having a high normal/iso aldehyde ratio.

DESCRIPTION OF THE PREFERRED EMBODIMENTS

The process of this invention involves the use, in combination, of both ethylene and an alpha olefinic hydrocarbon having from 3 to 20 carbon atoms as reactants in the low pressure oxo process. Such alpha olefinic compounds are characterized by a terminal ethylenic carbon-to-carbon bond which may be a vinylidene group, i.e., CH=C— or a vinyl group, i.e., CH$_2$=CH—. They may be straight-chain or branched-chain and may contain groups or substituents which do not essentially interfere with the course of the novel process. Such groups or substituents can be illustrated by carbonyl

oxy (—O—), hydroxy (—OH), carboxy (—COOH), halo, alkoxy, phenyl, haloalkyl, etc. The alpha olefinic compound can contain one ethylenic bond or it can contain more than one ethylenic bond. Illustrative alpha olefinic compound which can be employed as reactants include propylene, 1-butene, 1-pentene, 1-hexene, 1-heptene, 1-octene, 1-decene, 1-dodecene, 1-octadecene, 2-ethyl-1-hexene, styrene, 3-phenyl-1-propene, allyl chloride, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, 3-butenoic acid, 7-octenoic acid, 3-butenenitrile, 5-hexenamide and the like. Preferred alpha olefinic compounds include alkenes, alkyl alkenoates, alkenyl alkanoates, alkenyl alkyl ethers, and alkenols, especially those which contain up to 20 carbon atoms.

The catalysts used in the process of this invention consist essentially of rhodium in complex combination with carbon monoxide and ligand containing a trivalent atom of a Group VA element including phosphorus, arsenic and antimony, said trivalent atom possessing one available pair of electrons. The ligand can be a tertiary organo phosphorus compound, a tertiary organo arsenic compound or a tertiary organo antimony compound, and desirably wherein each organo moiety is composed of (1) carbon and hydrogen atoms, or (2) carbon, hydrogen and aliphatic etheric oxygen atoms, each of the organo moieties being monovalently bonded to the trivalent Group VA element through a carbon atom or an aliphatic etheric oxygen atom thereof. The organo moieties can also contain other substituents such as cyano and halo e.g., chloro. The term "aliphatic etheric oxygen atom" as used herein, is meant to convey the —O— group which does not form part of a heterocyclic ring such as, for example, dioxane. Consequently, the —O— groups present in, for instance, the trialkylphosphites or the triarylphosphites are considered, for purposes of our definition, to be "aliphatic etheric oxygen atoms". Strictly speaking, though, the oxygen atom in the trialkylphosphites and the triarylphosphites stem from the corresponding acid, i.e., phosphorous acid. As such various authorities consider the phosphite compounds to be esters. In its active form, the suitable complex catalysts will contain the rhodium component in a reduced valence state. The term "complex" as used herein including the claims, means a coordination compound formed by the union of one or more electronically rich molecules or atoms capable of independent existence with one or more electronically poor molecules or atoms, each of which is also capable of independent existence. The suitable ligands, as indicated above, possesses an element, i.e., phosphorus, arsenic or antimony, which has one available or unshared pair of electrons. When such elements have this electronic configuration it is capable of forming a coordinate bond with rhodium. The suitable ligands, as indicated above, possess an element, i.e., phosphorus, arsenic, or antimony, which has one available or unshared pair of electrons. When such elements have this electronic configuration it is capable of forming a coordinate bond with rhodium.

It is essential that the aforesaid ligands possess a $\Delta$HNP value of at least about 425, and preferabley at least about 500. By "$\Delta$HNP" is meant the difference in the half-neutralization potential between the ligand under consideration and N,N'-diphenyguanidine as determined according to the procedure act out in the article by C. A. Streuli, Analytical Chemistry, 32,985–987 (1960). The $\Delta$HNP value is a measure of the basicity of the ligand. For example, the relatively strong basic phosphorus-containing ligands such as those possessing a $\Delta$HNP value substantially below 425 gave complexes that were ineffective in the practice of the invention as evidenced by a lack of a discernible reaction rate and/or low normal to branched-chained aldehydic product isomer ratios. Those phosphorus-containing ligands which possessed a $\Delta$HNP value of at least about 425, and preferably at least about 500, are relatively less basic compounds. Complex catalysts prepared from such ligands effectively catalyzed the novel process whereby there resulted in a product mixture which contained a high normal to branched-chain aldehydic isomer ratio.

In Table A below, the $\Delta$HNP values of several illustrative phosphorus-containing ligands are set out.

TABLE A

| Ligand: | $\Delta$HNP[1] |
|---|---|
| $P(CH_3)_3$ | 114 |
| $P(C_2H_5)_3$ | 111 |
| $P(n-C_3H_7)_3$ | 115 |
| $P(n-C_4H_9)_3$ | 131 |
| $P(iso-C_4H_9)_3$ | 167 |
| $P(n-C_5H_9)_3$ | 139 |
| $P(2-n-C_4H_9OC_2H_4)_3$ | 162 |
| $P(2-C_6H_5C_2H_4)_3$ | 273 |
| $P(C_6H_{11})_3$ | 33 |
| $P(CH_3)(C_2H_5)_2$ | 117 |
| $P(CH_3)_2(C_2H_5)$ | 117 |
| $P(CH_3)_2(C_6H_5)$ | 281 |
| $P(C_2H_5)_2(C_6H_5)$ | 300 |
| $P(C_6H_{11})_2(2-CNC_2H_4)$ | 232 |
| $P(CH_3)_2(2-CNC_2H_4)$ | 291 |
| $P(n-C_4H_9)_2(2-CNC_2H_4)$ | 282 |
| $P(n-C_8H_{17})_2(2-CNC_2H_4)$ | 297 |
| $P(p-CH_3OC_6H_4)_3$ | 439 |
| $P(C_6H_5)_3$ | 573 |
| $P(C_6H_5)_2(C_2H_5)$ | 400 |
| $P(C_6H_5)_2(n-C_4H_9)$ | 400 |
| $P(O-n-C_4H_8)_3$ | 520 |
| $P(OCH_3)_3$ | 520 |
| $P(OC_6H_5)_3$ | 875 |

[1] E. M. Thorsteinson and F. Basolo J. Am. Chem. Soc. 88,3929–3936 (1966) C. A. Streuli, Analytical Chemistry, 32,985–987 (1960).

Aside from possible exceptions, it is apparent from a consideration of Table A supra that tertiary organo phosphorus-containing ligands in which at least two of the organo moieties are alkyl and/or cycloalkyl groups are excluded from the scope of the invention. Classes of ligands which are excluded, therefore, are the trialkylphosphines, the tricycloalkylphosphines, the mixed (alkyl) (cycloalkyl)phosphines, the dialkylarylphosphines, the diarylalkylphosphines, and the dicycloalkylarylphosphines.

By way of illustration, suitable classes of triorgano-containing ligands which are contemplated in the practice of the invention include the trialkylphosphites, the tricycloalkylphosphites, the triarylphosphites, the triarylphosphines, the triarylstibines, and the triarlyarsines. Desirably each organo moiety in the ligand does not exceed 18 carbon atoms. The triarylphosphites and the triarylphosphines represent the preferred classes of ligands. Specific examples of ligands which are suitable in forming the complex catalysts include trimethylphosphites, triethylphosphite, butyldiethylphosphite, tri-n-propylphosphite, tri-n-butylphosphite, tri-2-ethylhexylphosphite, tri-n-octylphosphite, tri-n-dodecylphosphite, triphenylphosphite, trinaphthylphosphite, triphenylphosphine, tri(p-chlorophenyl)phosphite, trinaphthylphosphine, phenyl diphenylphosphinite, diphenyl phenylphosphonite, diphenyl ethylphosphonite, triphenylarsine, triphenylstibine, tris (p-chlorophenyl)phosphine, tri(p-cyanophenyl)phiosphite, tri (p-methoxyphenyl) phosphite, ethyl diphenylphosphinite, and the like. Triphenylphosphite and triphenylphosphine are examples of the most preferred ligands. Such preferred ligands resulted in complex catalysts which effectively catalyzed alpha olefinic compounds at highly satisfactory reaction rates and also yielded high normal to branched-chain aldehydric product isomer ratios.

For the sake of convenience and brevity and primarily since the tertiary organo phosphorus compounds are the ligands of choice, the invention shall oftentimes be exemplified by continually referring to such phosphorus-containing compounds. As indicated previously, the trivalent phosphorus-containing ligand should have a ΔHNP value of at least about 425. Moreover, these ligands should be free of interfering or so-called sterically hindered groups. Ligands such as the triarylphosphines and the triaryl phosphites which are characterized by the presence of "bulky" groups, e.g., phenyl, tolyl, etc., in the ortho position of the aryl moieties have been observed to give catalyst complexes which are not preferred in the practice of the invention.

The process of this invention is effected in the presence of a catalytically significant quantity of the complex catalyst. The hydroformylation reaction will proceed when employing as little as about $1 \times 10^{-6}$ mol, and even lesser amounts, or rhodium (from the complex catalyst) per mol of olefins (total moles of ethylene and the higher olefin). However, such catalyst concentrations, though operable, are not particularly desirable since the reaction rate appears to be too slow and thus not commercially attractive. The upper catalyst concentration limit can be as high as about $1 \times 10^{-1}$ mol, and higher, of rhodium per mol of the olefins. However, the upper limit appears to be dictated and controlled more by economics in view of the high cost of rhodium metal and rhodium compounds. No particular advantages at such relatively high concentrations are manifest. A catalyst concentration of from about $1 \times 10^{-5}$ mol to about $5 \times 10^{-2}$ mol of rhodium metal per mol of the olefins is desirable. A concentration of from about $1 \times 10^{-4}$ to about $1 \times 10^{-2}$ mol of rhodium per mol of the olefins is preferred. Our observations generally indicate that optimum results are obtained by employing a catalyst concentration falling within the aforedefined preferred range. It is thus apparent that the concentration of the complex catalyst can vary over a rather wide range.

The concentration of ligand, e.g., the triorgano phosphorus ligand, to rhodium metal, on the other hand, is rather critical. Regardless whether one performs the active complex catalyst prior to introduction in the hydroformylation reaction zone or whether the active catalyst species is prepared in situ during the hydroformylation reaction, it is essential that the reaction be effected in the presence of free ligand. By "free ligand" is meant the tertiary organo Group VA compounds as exemplified by triphenylphosphite that are not tied to or complexed with the rhodium atom in the active complex catalyst. Though we do not wish to be held to any theory or mechanistic discourse, it appears that the active catalyst species contains, in its simplest form, a concentration of triorgano phosphorus ligand and carbon monoxide equal to a total of four mols in complex combination with one mol of rhodium. Thus, the active species may comprise a complex catalyst mixture, in their monomeric forms, which are characterized by one, two, and/or three triorgano phosphorus molecules complexed with one molecule of rhodium. As can be surmised from the above discussion, carbon monoxide (which incidentally is also properly classified as a ligand) is likewise present and complexed with the rhodium in the active species. In some instances, the active catalyst species may also contain hydrogen as a ligand. The ultimate composition of the active complex catalyst can be likened or attributable to the outcome of competing reactions between carbon monoxide and the triorgano phosphorus ligand for "complexing sites" with the rhodium element. These competing reactions can be disturbed or influenced, within significant limits, by increasing or decreasing the partial pressure due to carbon monoxide, or by increasing or decreasing the concentration of the triorgano phosphorus ligand. As a generalized statment, therefore, the component (carbon monoxide or triorgano phosphorus ligand) which can shift the equilibrium of the competing reaction in its favor should enjoy the greater opportunities of occupying the "complexing sites" with rhodium to give the active complex catalyst. One could view the function of free triorgano phosphorus ligand as either maintaining the status quo of the various forms of active complex catalyst during the hydroformylation, or as a means for shifting the equilibrium of the competing reactions in its favor and therefore causing additional triorgano phosphorus ligands to enter into complex combination with rhodium with the probable eviction of a similar number of carbon monoxide ligands from the complex catalyst.

In a desirable embodiment, the process of this invention is effected by employing a hydroformylation reaction mixture which contains at least about 2 mols of free triorgano phosphorus ligand per mole of rhodium. It is preferred that at least about 5 moles of free triorgano phosphorus ligand per mol of rhodium be employed. The upper limit does not appear to be narrowly critical and its concentration would be dictated largely by commercial and economic consideration. A preferred molar ratio of triorgano phosphorus ligand to rhodium is approximately 200:1.

Total pressures of carbon monoxide and hydrogen of less than about 450 p.s.i.a. and as low as one atmosphere, and lower, can be employed in the process of this invention with effective results. Total pressures of less than about 350 p.s.i.a. are preferred. A total pressure of carbon monoxide and hydrogen in the range of greater than about one atmosphere and less than about 250 p.s.i.a. is highly preferred since the unexpected and unobvious advantages discussed supra are readily attained when conducting our novel process at such low pressures. The savings in equipment costs is readily apparent also.

The preparation of the catalysts employed in the process of this invention is documented in the literature. A suitable method is to combine the rhodium salt of an organic acid with the ligand, e.g., triphenylphosphite, triphenylphosphine, etc., in liquid phase. The valence state of rhodium may the be reduced by hydrogenating the solution prior to the use of the catalyst therein. Alternatively, the catalysts may be prepared from a carbon monoxide complex of rhodium. For example, one could start with dirhodium octacarbonyl, and by heating this substance with the ligand, the ligand will replace one or more of the carbon monoxide molecules, thus producing the desired catalyst. It is also possible to start with the ligand of choice and rhodium metal; or an oxide or rhodium, and prepare the active catalyst species in situ during the hydroformylation reaction.

In the process of this invention the partial pressure attributable to carbon monoxide is desirably no great than about 75 percent of the total pressure of carbon monoxide and hydrogen. However, in certain instances it may be plausible to increase the carbon monoxide partial pressure to a value of above 75 percent of the total pressure of carbon monoxide and hydrogen, for instance, to about 80 percent or even 85 percent, by employing a very large excess of free triorgano phosphorus ligand; however, in such cases we would be departing somewhat from attaining a truly commercial operation. In general, a partial pressure attributable to hydrogen of from about 25 to 90 percent based on the total pressure of carbon monoxide and hydrogen is suitable.

The process of this invention can be conducted at temperatures as low as about 50° C. and up to 145° C. with advantageous results. A temperature in the range of from about 60° C. to about 125° C. is preferred. Within this preferred range maximum beneficial results are attained. Any mole ratio of ethylene to the higher olefin can be used, the preferable range being from 0.1:1 to 10:1

Solvents are not required in the practice of the invention but oftentimes their use is desirable and practical. One can employ normally-liquid organic solvents which are inert or which do not interfere to any substantial degree with the desired hydroformylation reaction under the operative conditions employed. Illustrative of such solvents include the saturated hydrocarbons, such as the pentanes, naphtha, kerosene, mineral oil, cyclohexane, etc. as well as the aromatic hydrocarbons, ethers, ketones, and nitriles as illustrated by benzene, xylene, toluene, diethyl ether, acetophenone, cyclohexanone, benzonitrile, and the like. One preferred class of solvents include the aldehydes to be produced in the given reaction. Another preferred class of solvents include the high boiling liquid aldehyde condensation products as illustrated by 2,2,4-trimethylpentandiol-1,3 monoisobutyrate. Commonly-assigned, co-pending U.S. patent application Ser. No. 556,270, filed Mar. 7, 1975, which is a continuation of abandoned U.S. patent application Ser. No. 887,370, filed Dec. 22, 1969, discloses the use of the high boiling liquid aldehyde condensation products as a reaction solvent for the catalyst.

By the term "higher boiling liquid aldehyde condensation products" as used herein is meant the complex mixture of high boiling liquid products which result from the condensation reactions of some of the aldehyde products of the process of the invention. Such condensation products can be preformed or produced in situ in the present process. The rhodium complex catalyst is soluble in these relatively high boiling liquid aldehyde condensation products while exhibiting excellent stability over extended periods of continuous hydroformylation. In a preferred form of the process of the invention the higher boiling liquid aldehyde condensation products to be used as solvents are preformed prior to introduction into the reaction zone and the startup of the process. It is also preferred to maintain the condensation products at about 5 to 50 weight percent based on the total weight of the reaction medium.

The process of this invention can be carried out in any suitable manner. By way of illustration, the hydroformylation process may be conducted in a continuous, semi-continuous, or batch fashion. The olefins can be premixed and added together or added separately to the reaction zone. The catalyst can be added to the hydroformylation zone batchwise, continuously, or incrementally. The aldehyde products can be recovered from the hydroformylation reaction product by any suitable means, for example, by gas stripping or by simple distillation. The aldehydes can then be separated from each other by conventional distillation. Recovered unused starting materials and solvents formed in situ can be returned to the reaction zone.

The unexpected features of the process of this invention include the high catalyst efficiency (meaning the unit weight of aldehyde produced in a given time per unit weight of catalyst) obtained by the coreaction of ethylene and an alpha olefinic hydrocarbon having from 3 to 20 carbon atoms in the low pressure oxo process to produce propionaldehyde in addition to and concurrently with a higher organic oxygenated compound comprising an aldehyde having a high normal-/iso aldehyde ratio. The simultaneous production of propionaldehyde and a higher organic oxygenated compound comprising an aldehyde having a high normal-/iso aldehyde ratio by the coreation of ethylene and an alpha olefinic hydrocarbon having from 3 to 20 carbon atoms is accomplished without reducing the production rate of the higher organic oxygenated compounds comprising aldehydes having a high normal/iso aldehyde ratio below the rate achieved when the higher olefin is reacted in the absence of the ethylene. Thus, the discovery of an unexpected and unobvious independence of the two reactions underlies the present invention. The high normal/iso aldehyde ratios characteristic of the low pressure oxo process as practiced in the prior art are also achieved in the co-reaction process of the present invention. Hence, more aldehyde production can be attained in a given production unit.

The following abbreviations are used in the Examples appearing below.

| ABBREVIATION | MEANING |
| --- | --- |
| lbs. | Pounds |
| ppm | Parts by weight per million by weight |
| TPP | Triphenylphosphine |
| °C. | Degree Centigrade |
| psi | Pounds per square inch |
| psig | Pounds per square inch gauge |
| psia | Pounds per square inch absolute |
| ΔHNP | Difference in half neutralization potential |
| g mol/l-hr | Gram moles/liter-hour |

The apparatus used for each of the following examples included a continuous stirred tank reactor. Four separate feed lines [consisting of propylene, ethylene, synthesis gas (carbon monoxide and hydrogen) and recycled gas] form a combined stream and enter the reactor. The reactor is equipped with a condenser for removing aldehydes and small amounts of byproducts from the reactor effluent, a liquid-vapor separator for removing the vaporous effluent to the gaseous recycle stream and recovering aldehyde products in a single product storage tank, and a cycle compressor for compressing and recycling the vaporous effluent back to the reactor. The gas recycle process used in this invention involved the supplying of olefins and synthesis gas (carbon monoxide and hydrogen) to the reactor, removing from the reactor a vaporous mixture comprising unreacted olefins, hydrogen, carbon monoxide, vaporized aldehyde products and vaporized aldehyde condensation products essentially equal to the rate of their formation in the reactor, recovering aldehyde products and aldehyde condensation products from said vaporous mixture and returning the remainder of the vaporous mixture via a gaseous recycle stream back to the reactor. The apparatus used and the gas recycle process used in the examples are further illustrated by reference to Belgium Pat. No. 853,377. istic of the low pressure oxo process, was maintained. The day by day log is shown in Table A below.

TABLE A

| Days of Operation | 1 | 2 | 3 | 4 | 5 | 6 | 7 | 8 | 9 | 10 |
|---|---|---|---|---|---|---|---|---|---|---|
| Operating Conditions | | | | | | | | | | |
| Reactor Feed[1] | 6377 | 6363 | 7140 | 7206 | 7095 | 7258 | 7478 | 7561 | 7746 | 8374 |
| Blow-off Flow[2] | 232 | 229 | 232 | 258 | 251 | 274 | 247 | 170 | 158 | 226 |
| Reactor Temperature, °C. | 110 | 110 | 110 | 110 | 110 | 110 | 110 | 110 | 110 | 110 |
| Reactor Pressure, PSIG | 180 | 180 | 180 | 180 | 180 | 180 | 180 | 180 | 180 | 180 |
| Partial Pressures, PSIA | | | | | | | | | | |
| $H_2$ | 95 | 91 | 98 | 98 | 99 | 99 | 90 | 83 | 83 | 84 |
| CO | 10 | 9 | 9 | 9 | 10 | 10 | 10 | 9 | 10 | 14 |
| $C_2H_4$ | 1.5 | 1.5 | 1.4 | 1.6 | 1.7 | 1.5 | 1.9 | 1.9 | 1.5 | 1.7 |
| $C_3H_4$ | 26 | 26 | 25 | 27 | 25 | 25 | 29 | 31 | 31 | 28 |
| Reactor Performance | | | | | | | | | | |
| Reaction Rates, g mol/l-hr | | | | | | | | | | |
| Propionaldehyde | 4.7 | 4.7 | 4.5 | 5.0 | 4.9 | 4.8 | 4.9 | 4.8 | 4.6 | 4.9 |
| i-Butyraldehyde | 0.1 | 0.1 | 0.2 | 0.1 | 0.1 | 0.1 | 0.1 | 0.1 | 0.1 | 0.2 |
| n-Butyraldehyde | 1.9 | 1.8 | 2.1 | 2.0 | 1.9 | 2.0 | 2.0 | 2.0 | 1.9 | 1.7 |
| Isomer Ratio, normal/iso | 18 | 18 | 12 | 15 | 16 | 14 | 16 | 15 | 17 | 10 |

[1]Reactor feed is measured in units of standard cubic feet per hour.
[2]Blow-off Flow is defined as the gas flow in standard cubic feet per hour of unreacted materials and by-products (propane, ethane) coming out of the system and not recycled.

The following examples illustrate the present invention:

EXAMPLE I

To a 100 gallon tank reactor was added 127 liters of solution comprised of 270 ppm rhodium as rhodium carbonyl 2,4-pentanedionato triphenylphosphine, 14 weight percent triphenylphosphine, 50 weight percent 2,2,4-trimethylpentanediol-1,3 monoisobutyrate and the remainder propionaldehyde. The temperature in the reactor was 110° C. Ethylene, CO and $H_2$ feeds were started to the reactor to maintain partial pressures in the vapor space of 95 psi $H_2$, 10 psi CO, and 1.5 psi ethylene. $C_2H_6$ and $C_3H_8$ entered the reactor as impurities in the olefin feed and also as byproducts of the reaction. $CH_4$ entered the reactor at this time as an impurity of the (CO+$H_2$) synthesis gas. As soon as the production of propionaldehyde started and the gas recycle stabilized, propylene feed was started to the reactor maintaining a propylene partial pressure of 26 psi. Small amounts of butyraldehydes and propionaldehyde also entered the reactor via the recycle gas system. At steady state the gaseous feed to the reactor consisted of the following components on a volume percent basis:

| | |
|---|---|
| $C_3H_6$ | 13.7 |
| $C_2H_4$ | 8.3 |
| $H_2$ | 49.3 |
| CO | 16.2 |
| $CH_4$ | 2.5 |
| $C_2H_6$ | 4.2 |
| $C_3H_8$ | 3.0 |
| Butyraldehydes | 0.3 |
| Propionaldehyde | 2.5 |

During the course of the reaction, the high boiling liquid aldehyde condensation products formed and served as a solvent for the reaction. The reaction rate for butyraldehydes was 2.0 gram moles per liter-hour [the same rate expected without ethylene feed which is equivalent to 12,241 lbs. aldehyde/(day) (lb. of contained Rhodium)] and for propionaldehyde was 4.7 gram moles per liter-hour for a total catalyst efficiency of 37,032 lbs. aldehyde/(day) (lb. of contained Rh). This reaction rate was successfully maintained for a period of ten days. Also, a high normal/iso butyraldehyde ratio, character-

EXAMPLE II

Part A: Propylene

To a 100 gallon stirred tank reactor was added 189 liters of solution comprised of 270 ppm rhodium as rhodium carbonyl 2,4-pentanedionato triphenyphosphine, 13.7 percent triphenylphoshine, with the remainder of the solution comprised of mixed butyraldehyde condensation products exemplified by 2,2,4-trimethylpentanediol-1,3 monoisobutyrate and butyraldehydes. Propylene, CO and $H_2$ feeds were started to the reactor to maintain partial pressures in the vapor space of 38 psi $H_2$, 9.2 psi CO and 23.9 psi propylene. The temperature in the reactor was 110° C. The reaction rate for butyraldehydes was 1.1 gram moles per liter-hour under these conditions. This equates to a catalyst efficiency of 7,845 lbs. of aldehyde/(day) (lb. of contained Rh). This reaction rate was maintained for a period of four days.

Part B: Propylene+Ethylene

To a 100 gallon stirred tank reactor was added 189 liters of solution comprised of 270 ppm rhodium as rhodium carbonyl 2,4-pentanedionato triphenylphosphine, 13.7 percent triphenylphosphine, with the remainder of the solution predominantly 2,2,4-trimethylpentanediol-1,3 monoisobutyrate and butyraldehyde. Propylene, CO and $H_2$ feeds were started to the reactor to maintain partial pressures in the vapor space of 38 psi $H_2$, 9.2 psi CO, and 23.9 psi propylene. As soon as the production of butyraldehyde started and the gas recycle stabilized, ethylene feed was started to the reactor maintaining a partial pressure of 0.5 psi. The temperature in the reactor was 110° C. The reaction rate for butyraldehydes was 1.1 gram moles per liter-hour (the same rate obtained without ethylene feed in Example II, Part A) and for propionaldehyde was 1.2 gram moles per liter-hour for a catalyst efficiency of 14,700 lbs. of aldehyde/(day) (lb. of contained Rh). This reaction rate was successfully maintained for a period of four days.

What is claimed is:

1. In a process for the production of oxygenated products comprising aldehydes having a high normal/iso aldehyde ratio which process comprises (1) forming a reaction mixture containing (a) an alpha olefinic hydrocarbon having from 3 to 20 carbon atoms; (b)

carbon monoxide; (c) hydrogen; (d) a catalytic quantity of a complex catalyst consisting essentially of rhodium in complex combination with (i) carbon monoxide and (ii) a triorgano phosphorus ligand of the group consisting of trialkylphosphites, tricycloalkylphosphites, triarylphosphites, and triarylphosphines; each organic moiety thereof having up to 18 carbon atoms; and said triorgano phosphorus ligand possessing a Δ HNP value of at least about 425; and (e) at least 2 moles of free ligand as defined above per mole of rhodium; (2) maintaining the reaction mixture at a temperature in the range of from about 50° C. to 145° C.; at a total pressure of carbon monoxide and hydrogen of less than 450 psia, and a partial pressure attributable to carbon monoxide no greater than about 75 percent of said total pressure; thereby (3) reacting said olefinic hydrocarbon with said carbon monoxide and hydrogen with the formation of said oxygenated products comprising aldehydes having a high normal/iso aldehyde ratio, the improvement which consists in including in said reaction mixture ethylene and additional carbon monoxide and hydrogen in amounts at least sufficient to react with said ethylene and reacting said ethylene with said carbon monoxide and hydrogen with the formation of propionaldehyde in addition to and concurrently with said oxygenated products comprising aldehydes having a high normal-/iso aldehyde ratio.

2. A process as claimed in claim 1 wherein the ratio of ethylene to the olefinic hydrocarbon containing from 3 to 20 carbon atoms is from 0.1:1 to 10:1.

3. A process as claimed in claim 1 wherein the olefinic hydrocarbon containing from 3 to 20 carbon atoms is propylene.

4. A process as claimed in claim 1 wherein the olefinic hydrocarbon containing from 3 to 20 carbon atoms is butylene.

5. A process as claimed in claim 1 wherein the reaction of the ethylene and the propylene is conducted in high boiling liquid aldehyde condensation products formed during the reaction.

* * * * *